United States Patent [19]

Malek et al.

[11] Patent Number: 4,603,252
[45] Date of Patent: Jul. 29, 1986

[54] DETERMINATION OF THE INTEGRITY OF PART OF STRUCTURAL MATERIALS

[75] Inventors: Samir Malek, Schwanewede-Leuchtenburg; Bernd Hofer, Lemwerder, both of Fed. Rep. of Germany

[73] Assignee: Messerschmitt-Boelkow-Blohm GmbH, Bremen, Fed. Rep. of Germany

[21] Appl. No.: 549,393

[22] Filed: Nov. 7, 1983

[30] Foreign Application Priority Data

Nov. 20, 1982 [DE] Fed. Rep. of Germany ....... 3243026
May 10, 1983 [DE] Fed. Rep. of Germany ....... 3317051

[51] Int. Cl.$^4$ ................................................ H01J 5/16
[52] U.S. Cl. ...................................... 250/227; 73/800
[58] Field of Search .................. 73/800; 250/227, 221; 65/29; 340/550, 545, 555

[56] References Cited

U.S. PATENT DOCUMENTS

| | | | |
|---|---|---|---|
| 3,910,105 | 10/1975 | Hoffstedt | 65/29 |
| 3,943,021 | 3/1976 | Lindsey | 350/96.1 |
| 4,221,962 | 9/1980 | Black et al. | 250/227 |
| 4,367,460 | 1/1983 | Hodara | 250/221 |

*Primary Examiner*—David C. Nelms
*Assistant Examiner*—Michael Messinger
*Attorney, Agent, or Firm*—Ralf H. Siegemund

[57] ABSTRACT

Laminated parts of structural material receive as embedment light transmitting fibers, preferably in addition to reinforcing fibers, and light transmission through the light transmitting fibers is monitored for purposes of determining pattern irregularities and formation of cracks.

7 Claims, 2 Drawing Figures

U.S. Patent    Jul. 29, 1986    4,603,252
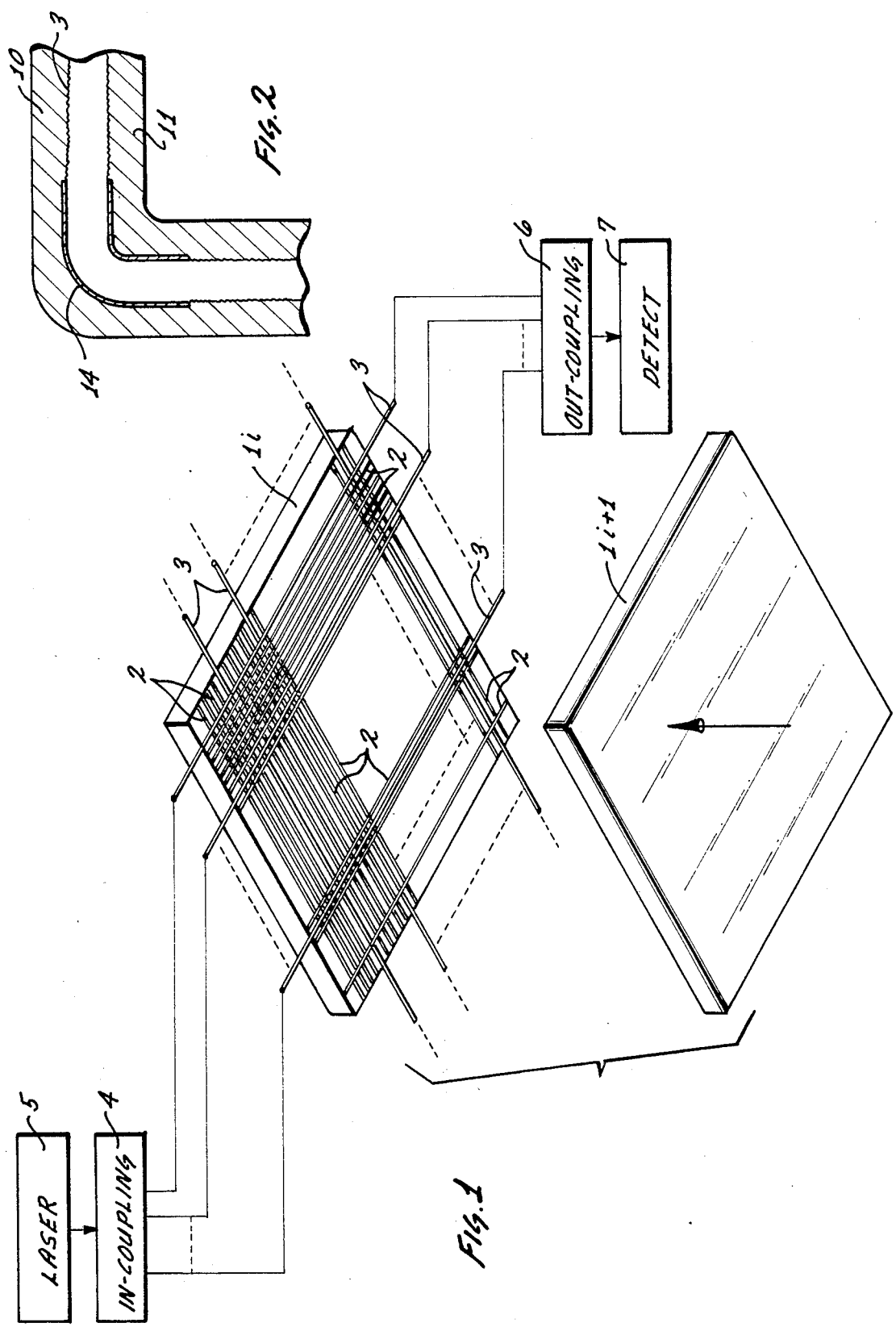

DETERMINATION OF THE INTEGRITY OF PART OF STRUCTURAL MATERIALS

BACKGROUND OF THE INVENTION

The present invention relates to the measurement and determination of the integrity of test objects such as components of structural material.

In our copending application Ser. No. 438,864, we have proposed a method and device for the determination and detection of cracks in test objects whereby light conducting fibers such as synthetic fibers, glass fibers or quartz fibers are attached to the surface of a test object. Through appropriate coupling techniques light is transmitted into one end of these fibers and the transmission of that light is monitored at the respective other end of each and all of the fibers. Thus, the monitoring process proper relates to monitoring the transmission of light through these fibers. Any crack in the test object will cause the respective fiber or fibers above to crack likewise causing a drastic reduction in light transmission through the respective fiber. This reduction is detected and used as indication for the occurence of a crack. The method particularly is advantaged by the fact that the crack formation is irreversible, particularly as far as the fibers are concerned. Thus, cracks in a component of a structural material may hardly be detectable as such after for example the overload causing the crack has decayed. However, a crack in such a glass fiber reduces the light transmission therethrough even if the bounding surfaces of the crack abut very closely; the transmission characteristic is irreversibly altered and remains permanently available as an indication that indeed a local crack was produced.

DESCRIPTION OF THE INVENTION

It is a primary object of the invention to expand on the concept expounded above and to improve the versatility of employment. In accordance with a primary feature of the invention it is suggested to embed light transmitting fibers in the interior of a component made of a structural material. In this regard it is another feature of the invention to embed light conducting fibers as separate layers within the configuration of a component of structural material being of laminated configuration wherein particularly the glass fibers are arranged in between adjacent laminas.

The configuration above serves in the completed component as indicator of the formation of internal cracks, local delamination or the like. However, in accordance with the expanded concept of the invention the glass fibers should be embedded or included with a certain degree of regularity that reflects the desired internal structure and its regularities of the part to be made.

It is therefore a particular feature of the present invention to use the glass fibers already as embedded within a laminated construction for monitoring the production and manufacture of the part to be made. If the part, as it is being made through multiple laminations, is to include a regular pattern of such light transmitting fibers, that regularity may be disturbed if during the manufacturing process certain irregularities occur which are per se not visible from the outside. Moreover, individual fibers may already be damaged during the manufacture so that in toto, the light transmission does not exhibit the degree of desired regularity to be detected already during or immediately after the manufacture.

Therefore, it is an object of the present invention to provide also for a reliable monitoring and supervision of the manufacturing process under utilization of embedded light conducting fibers. Accordingly, these light conducting fibers are embedded and included in between several of the laminas of a laminated part as it is being made and after, for example, curing of the synthetic material of which the laminas consists one obtains a visible indication of the fiber texture and any change from a desired pattern.

The invention is to be used with particular advantage in those instances in which the component of structural material is not only made of synthetic laminas but if the part is to be reinforced through fibers, for example, carbon fibers or the like. In this case, light transmitting fibers are to be included within the pattern of reinforcing fibers. If, for example, these fibers generally are arranged in a grid or mesh pattern, included light transmitting fibers reflect that pattern as such. If monitored through transmission of light, one obtains a direct indication of the pattern i.e. grid regularity or lack thereof. For example, such a component may be subjected to press working which in cases may result in an undesirable shift in the reinforcing fibers. Since the light transmitting fibers will correspondingly be shifted, this internal disturbance and pattern distortion can now be readily be detected through monitoring the light transmission through the light transmitting fibers. In fact, the monitoring process can be carried out during the press working, and if a distortion is impending appropriate steps may be taken in the control of the press working to avoid, if at all possible, pattern changes in the reinforcing fiber structure and texture. In some cases the fibers which are embedded as reinforcing fibers are glass fibers which can now be used directly for purposes of monitoring the structure as a whole. In the case of fiber reinforced synthetic, so-called prefab material can be used but should include light transmitting fibers for the inventive purpose.

In furtherance of the invention it may be of advantage to provide the light transmitting fibers with a certain degree of surface roughness. This feature enhances adhesion to the surrounding synthetic material but also it establishes microscopic notches in the surface of the respective light transmitting fibers which, in fact, reduce the elastic limit and cause earlier rupture in case of undue loads; this feature was found to increase the sensitivity of the detection of the formation of cracks in the interior of the part being supervised and monitored. The roughness may be provided through etching or the like.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is an exploded view of a portion of a part of structural material in combination with the equipment for monitoring the structural integrity of the part in accordance with the preferred embodiment for practicing the best mode thereof; and FIG. 2 is an enlarged view of a portion of a different part of structural material.

Proceeding now to the detailed description of the drawings, $1i$ and $1i+1$ denote generally two laminas pertaining to a multiple laminas part of a structural material being of laminated construction accordingly. Moreover, a plurality of reinforcing fibers, for example carbon fibers 2, are arranged in a grid pattern to be interposed between these two laminas $1i$ and $1i+1$. These carbon fibers are, for example, arranged in a regular pattern for reasons of subsequent employment of the part. Now, in accordance with the present invention, light conducting fibers are included in this grid pattern and together these light conducting fibers 3 establish a corresponding pattern of their own accord. The regularity of this grid pattern of light conducting fibers reflects the regularity of the reinforcing fibers 2.

Assume for one set of these light conducting fibers, one end thereof is connected to a coupling structure 4 being appropriately connected, for example, to a laser light source 5 for purposes of providing sufficiently intense conduction of light. The other end of these fibers 3 are connected to a coupling network or structure 6 cooperating with a detector 7 or a set of detectors. The light generation and coupling structures as well as the pickup monitoring and detecting operations can be provided as disclosed in a variety of configurations in our above identified copending application, the content of which is incorporated by reference for that purpose.

Generally speaking, these various light conducting fibers 3 may be cyclically individually interrogated through selective coupling of the detector to the various ends for serially receiving light that passes through these fibers 3 as a serial pattern reflects the regularity of the fiber pattern at large. For example, a shifting of reinforcing fibers within the pattern entails a shift in the light transmitting fibers during the manufacturing process of the part which leads to tensioning and expansion or even rupture of one or the other light transmitting fiber which is directly indicated as a variation in the light transmissivity of the respective fiber or fibers.

FIG. 2 shows by way of example a light conducting fiber 13 in between two parts 10 and 11 having by its nature a corner. It is advisable in these cases to cover the fiber 13 in the area of bending with a protective cover 14 which prevents fracture of the fiber in that location except in very severe circumstances, but permits the bending of the fiber without change in transmissivity, i.e. without rupture. The zone thus protected can be very small. Moreover, this Figure shows that the surface of the glass fiber is slightly rough in order to enhance adhesion of the fiber to the parts 10 and 11. The cover portion of the glass fiber may not be roughened in order to enhance sensitivity of the structure outside of the bent area. This, then demonstrates the feature of limiting the sensitivity of the light conducting fibers to certain zones or area by locally roughening the surface while covering the other portion in which no crack sensitivity is needed or desired with no protective cover.

A cover such as 14 may be provided generally on top of the fiber before exposing the fiber to the roughness producing etch fluid. Therefore, the cover may alternatively or additionally provide the function of limiting application of surface roughness to certain zones of the fiber. In the illustrated case, of course, the cover 14 provides additionally a protection against fiber cracking during bending when applied. Moreover, it should be mentioned that the aspects of increasing surface roughness either over the entire surface of the glass fiber or in selected surface zones, is applicable to surface crack detections of metal and other parts as per our copending application.

The invention is not limited to the embodiments described above, but all changes and modifications thereof, not constituting departures from the spirit and scope of the invention are intended to be included.

We claim:

1. A method for monitoring the integrity of a laminated part of structural material prior to use comprising the steps of:
    including a plurality of light conducting fibers in at least one layer in between adjacent laminas of the part and in a regular pattern; and
    determining the regularity of light transmission of said fibers within the part and as resulting from the pattern, under utilization of intense light, at least after completion of the manufacture of the part, so as to obtain a visible indication of any distortion of that pattern on account of shifting of the fibres relative to each other.

2. A method as in claim 1 where the laminas are made of synthetic material, the laminated part being cured subsequent to the embedding of the light conducting fibers.

3. A method as in claim 1 including providing a grid or mesh like pattern for the light conducting fibers.

4. A method as in claim 1 wherein reinforcing fibers are placed in between laminas, said light transmitting fibers being included in the arrangement of reinforcing fibers.

5. The method as in claim 1 and including the step of arranging the fibers within an arrangement of reinforcing fibers.

6. The method as in claim 1 and including the step of providing said transmitting fibers, over at least portions of their surface, with a surface roughness for enhancing adhesion to the respective laminas.

7. The method as in claim 6 and including the step of covering a portion of at least some of the light transmitting fibers with a protective cover.

* * * * *